(12) United States Patent
Srinivasan et al.

(10) Patent No.: US 11,468,999 B2
(45) Date of Patent: Oct. 11, 2022

(54) SYSTEMS AND METHODS FOR IMPLEMENTING DENSITY VARIATION (DENSVAR) CLUSTERING ALGORITHMS

(71) Applicant: Accenture Global Solutions Limited, Dublin (IE)

(72) Inventors: Karthik Srinivasan, Dharmapuri (IN); Deepak A. Sharma, Bengaluru (IN); Romesh Viswanath, Hyderabad (IN); Ram Mohen Venkatakrishnan, Bengaluru (IN); Ramanan Ramanathan, Hyderabad (IN)

(73) Assignee: Accenture Global Solutions Limited, Dublin (IE)

( * ) Notice: Subject to any disclaimer, the term of this patent is extended or adjusted under 35 U.S.C. 154(b) by 0 days.

(21) Appl. No.: 16/945,170

(22) Filed: Jul. 31, 2020

(65) Prior Publication Data

US 2022/0037033 A1  Feb. 3, 2022

(51) Int. Cl.
*G06F 16/28* (2019.01)
*G16H 50/80* (2018.01)
*G06F 16/29* (2019.01)

(52) U.S. Cl.
CPC ........... *G16H 50/80* (2018.01); *G06F 16/285* (2019.01); *G06F 16/288* (2019.01); *G06F 16/29* (2019.01)

(58) Field of Classification Search
CPC ..... G16H 50/80; G06F 16/288; G06F 16/285; G06F 16/29
USPC ......................................................... 706/45
See application file for complete search history.

(56) References Cited

U.S. PATENT DOCUMENTS

| | | | |
|---|---|---|---|
| 2013/0060775 A1* | 3/2013 | Qiu | G16B 40/00 707/737 |
| 2017/0103121 A1* | 4/2017 | Mori | G06F 16/287 |
| 2017/0270365 A1* | 9/2017 | Laska | G06F 3/04845 |
| 2018/0012463 A1* | 1/2018 | Chaudhry | H04N 7/181 |
| 2019/0042893 A1* | 2/2019 | Kafai | G06K 9/00 |
| 2019/0102889 A1* | 4/2019 | Azanza | H04N 19/543 |
| 2019/0170519 A1* | 6/2019 | Anwar | G06F 16/29 |
| 2019/0197136 A1* | 6/2019 | Meron | G06F 16/285 |
| 2020/0012937 A1* | 1/2020 | Walters | G06F 16/285 |
| 2020/0260052 A1* | 8/2020 | Hutchinson | A61B 5/113 |
| 2020/0320430 A1* | 10/2020 | Kunnumma | G06K 9/6267 |

(Continued)

*Primary Examiner* — Tamara T Kyle
*Assistant Examiner* — Raheem Hoffler
(74) *Attorney, Agent, or Firm* — Norton Rose Fulbright US LLP

(57) ABSTRACT

The present disclosure provides a clustering device configured to detect varying density. The clustering device may receive a set of parameters (e.g., a density parameter specifying a plurality of density values, a size parameter, and a node parameter that includes information associated with a plurality of nodes) for identifying clusters. The clustering device may determine a distance between different pairs of nodes of the plurality of nodes and identify candidate nodes of the plurality of nodes based on the distance determined for the different pairs of nodes and the size parameter. Candidate nodes may be assigned to a candidate cluster that may be evaluated against the density parameter to determine whether a density of the candidate cluster satisfies at least one of the plurality of density values. A cluster may be identified based on whether the candidate cluster satisfies at least one of the plurality of density values.

20 Claims, 7 Drawing Sheets

(56) References Cited

U.S. PATENT DOCUMENTS

2020/0321076 A1* 10/2020 Putnam .................. G16B 20/20
2020/0387860 A1* 12/2020 Mohamed ............... G06F 16/29
2020/0410029 A1* 12/2020 Bastide .................. G06F 16/29
2021/0027503 A1* 1/2021 Kumaresan ............. G06F 16/26

* cited by examiner

SYSTEMS AND METHODS FOR IMPLEMENTING DENSITY VARIATION (DENSVAR) CLUSTERING ALGORITHMS

TECHNICAL FIELD

The present application relates to clustering algorithms and more specifically to clustering algorithms that may be leveraged to rapidly identify clusters with varying densities.

BACKGROUND

Various clustering algorithms exist, such as DBSCAN, HDBSCAN, and K-means clustering algorithms. While such algorithms have proved useful for some use cases, they suffer from some drawbacks that limit their utility for other use cases. One known limitation of existing clustering algorithms is their inability to identify clusters based on different density levels. For example, to identify clusters having different density levels, existing clustering algorithms need to be executed multiple times, each execution seeking to identify a cluster or clusters having a density associated with that execution, but cannot identify clusters with different densities in a single execution. Such processing is computationally inefficient and slow, which may limit utilization of such techniques for applications and use cases for which rapid processing may be important. Additionally, existing clustering algorithms may not be utilized with large databases (e.g., large datasets), which may limit or prevent their use with certain datasets and use cases.

SUMMARY

The present application discloses systems, methods, and computer-readable storage media for rapid identification of clusters of varying densities from among an input data set. A clustering device implementing clustering algorithms according to aspects of the present disclosure may receive a set of parameters for identifying clusters. The set of parameters may include a density parameter specifying a plurality of density values (e.g., an array minPts[ ] of density values), a size parameter, and a node parameter (e.g., a data structure that includes information associated with a plurality of nodes). The clustering device may determine a distance between different pairs of nodes of the plurality of nodes and identify candidate nodes of the plurality of nodes based on the distance determined for the different pairs of nodes and the size parameter. Candidate nodes may be assigned to a candidate cluster that may be evaluated against the density parameter to determine whether a density of the candidate cluster satisfies at least one of the plurality of density values. A cluster may be identified based on whether the candidate cluster satisfies at least one of the plurality of density values. Additional clusters may also be identified, which may have the same density as the identified cluster or different densities.

The DENSVAR clustering algorithms utilized by the clustering devices disclosed herein may provide functionality for rapid identification of clusters from among a data set, which may be particularly beneficial for many use cases to which the clustering algorithms of embodiments may be applied. For example, the clustering device may detect hot spots associated with spread of an infectious disease by identifying clusters of persons infected by the disease. The different densities of the identified clusters may be used to present data to users that enables those users to identify areas where there is high risk of coming into contact with the infectious disease and enable them to plan their travel in a manner designed to avoid or minimize their risk of exposure. The different densities of the identified clusters may enable user applications to graphically represent the clusters and their associated densities, such as by coloring clusters having a high density of the disease in a first color (e.g., red), clusters having a moderate density of the disease in a second color (e.g., yellow), clusters having a low density of the disease in a third color (e.g., green). Additionally, the clustering device may transmit notifications to third parties to inform them of characteristics of density clusters in proximity to the third parties. For example, the clustering algorithms may be utilized to monitor spaces for compliance with social distancing guidelines and transmit notifications to one or more individuals to inform them that social distancing practices are not being observed based on observed cluster characteristics.

The disclosed DENSVAR clustering algorithms may also be applied to other non-infectious disease related use cases, such as use cases related to traffic monitoring, consumer demand and logistics applications, and network optimization and planning. Clustering devices configured to utilize the clustering algorithms disclosed herein may be configured to handle diverse input data sets, which may include media content (e.g., video camera feeds, images, etc.), global positioning system (GPS) data, communication device signals, or other types of information to analyze and identify clusters relevant to a particular use case. The disclosed clustering algorithms are capable of identifying clusters having different densities, sizes, and shapes as part of a single process, thereby enabling the disclosed clustering algorithms to more rapidly process complex and large data sets as compared to previous clustering algorithms, such as DBSCAN and HDBSCAN algorithms, which are limited to identification of clusters with a single density per execution cycle. Such capabilities may enable the clustering algorithms disclosed herein to be more readily utilized for some use cases where real-time or near real-time processing may be important, such as traffic monitoring and infectious disease related use cases.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the disclosed methods and apparatuses, reference should be made to the implementations illustrated in greater detail in the accompanying drawings, wherein.

It should be understood that the drawings are not necessarily to scale and that the disclosed embodiments are sometimes illustrated diagrammatically and in partial views. In certain instances, details which are not necessary for an understanding of the disclosed methods and apparatuses or which render other details difficult to perceive may have been omitted. It should be understood, of course, that this disclosure is not limited to the particular embodiments illustrated herein.

DETAILED DESCRIPTION

Embodiments of the present disclosure provide systems, methods, and computer-readable storage media implementing improved clustering algorithms, that are capable of rapidly identifying clusters having different densities. The ability to identify density varying clusters may enable the disclosed clustering algorithms to more easily process large and complex data sets. Additionally, the clustering algorithms of embodiments may reduce the computational complexity of developing applications that address various use cases to which clustering algorithms are particularly suited, such as monitoring the spread of infectious diseases (e.g., COVID-19), traffic monitoring, communication network monitoring, consumer demand and order fulfillment logistics, weather pattern analysis, and the like. Additionally, the disclosed clustering algorithms may enable more rapid analysis of cluster characteristics, which may enable the clustering algorithms to be applied to data sets in a manner that provides real-time or near real-time feedback to users. Additional details and advantages of the disclosed clustering algorithms and the use cases to which the clustering algorithms may be applied are described in more detail below.

Figure 1:
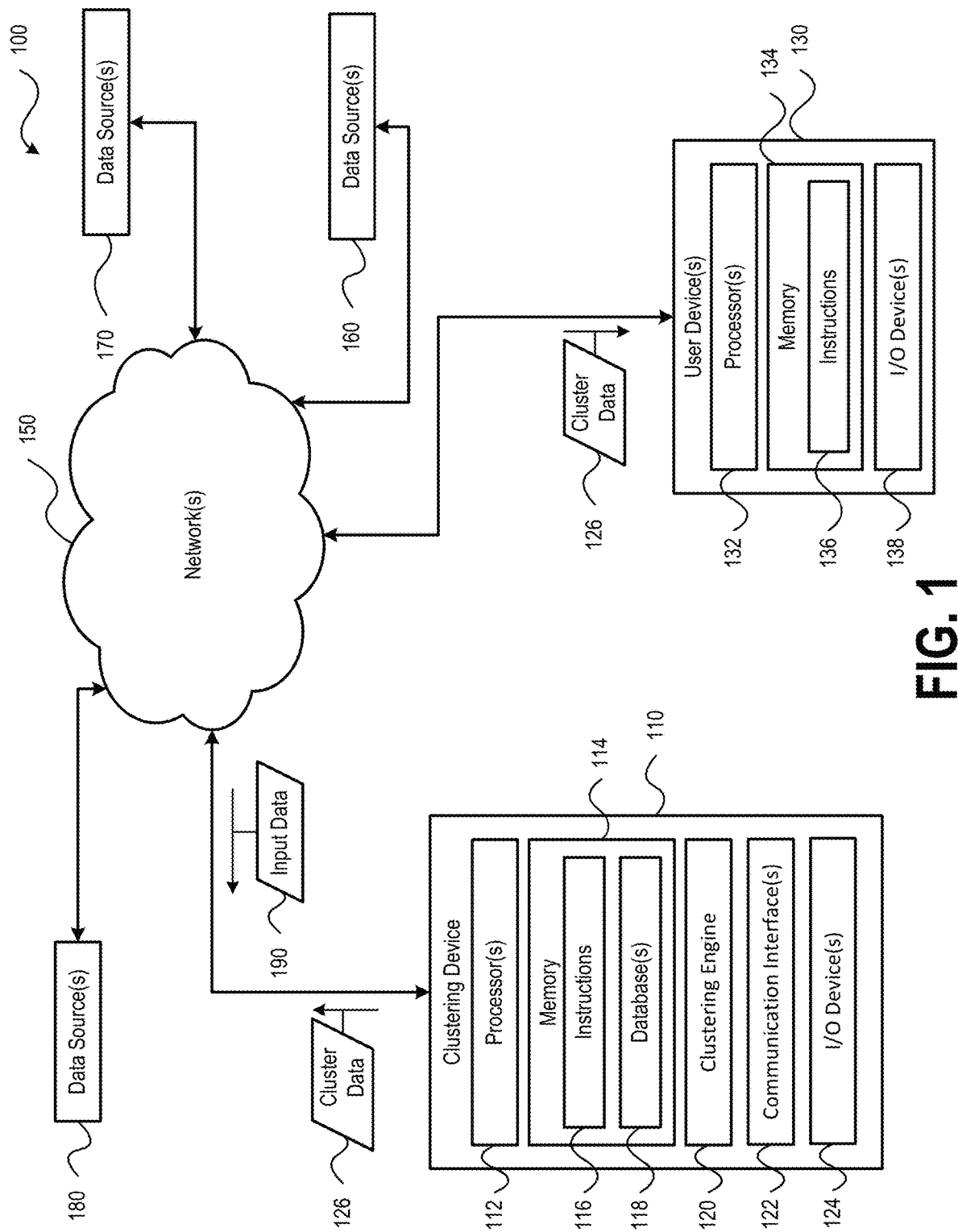
FIG. 1 is block diagram illustrating aspects of a system for identifying clusters having varying densities in accordance with embodiments of the present disclosure.

Referring to FIG. 1, a system providing functionality that leverages density variation (DENSVAR) clustering algorithms to support applications in accordance with embodiments of the present disclosure is shown as a system 100. The system 100 may be configured to identify clusters having varying densities from an input data set. The identified clusters may then be analyzed and data or characteristics of the identified clusters may be output to support various user-facing applications designed to address various use cases where clustering characteristics may be used to provide meaningful information to users, as will become apparent from the description below.

As shown in FIG. 1, the system 100 includes a clustering device 110. The clustering device 110 includes one or more processors 112, a memory 114, a clustering engine 120, one or more communication interfaces 122, and one or more input/output (I/O) devices 124. The one or more processors 112 may include one or more microcontrollers, application specific integrated circuits (ASICs), field programmable gate arrays (FPGAs), central processing units (CPUs) and/or graphics processing units (GPUs) having one or more processing cores, or other circuitry and logic configured to facilitate the operations of the clustering device 110 in accordance with aspects of the present disclosure. The memory 114 may include random access memory (RAM) devices, read only memory (ROM) devices, erasable programmable ROM (EPROM), electrically erasable programmable ROM (EEPROM), one or more hard disk drives (HDDs), one or more solid state drives (SSDs), flash memory devices, network accessible storage (NAS) devices, or other memory devices configured to store data in a persistent or non-persistent state. Software configured to facilitate operations and functionality of the clustering device 110 may be stored in the memory 114 as instructions 116 that, when executed by the one or more processors 112, cause the one or more processors 112 to perform the operations described herein with respect to the clustering device 110, as described in more detail below. Additionally, the memory 114 may be configured to store one or more databases 118. Exemplary aspects of the one or more databases 118 are described in more detail below.

The one or more communication interfaces 122 may be configured to communicatively couple the clustering device 110 to external devices and systems via one or more networks 150. The external devices and systems may include one or more user devices 130 and data sources 160, 170, 180, which are described in more detail below. Communication between the clustering device 110 and the external devices and systems via the one or more networks 150 may be facilitated via wired or wireless communication links established according to one or more communication protocols or standards (e.g., an Ethernet protocol, a transmission control protocol/internet protocol (TCP/IP), an Institute of Electrical and Electronics Engineers (IEEE) 802.11 protocol, and an IEEE 802.16 protocol, a 3rd Generation (3G) communication standard, a 4th Generation (4G)/long term evolution (LTE) communication standard, a 5th Generation (5G) communication standard, and the like). The one or more input/output (I/O) devices 124 may include one or more display devices, a keyboard, a stylus, one or more touchscreens, a mouse, a trackpad, a camera, one or more speakers, haptic feedback devices, or other types of devices that enable a user to receive information from or provide information to the clustering device 110.

The clustering engine 120 may be configured to determine clusters based on a set of parameters. The set of parameters may include a density parameter specifying one or more cluster densities. As an example, the density parameter may comprise an array (e.g., minPts[ ]) that specifies minimum numbers of affected people required to identify a cluster for a use case utilizing the disclosed clustering algorithm to identify hot spots associated with an infectious disease, such as COVID-19. Notably, the array may specify different minimum numbers of affected people to identify clusters having different densities, where each different density may be indicative of a risk level of coming into contact with someone infected by COVID-19. To illustrate, the density parameter array may include a first value identifying a first number of affected people associated with a high risk level (e.g., a high risk level of coming into contact with a person infected with COVID-19), a second value identifying a second number of affected people associated with a second risk level (e.g., a moderate risk level of coming into contact with a person infected with COVID-19), and a third value identifying a third number of affected people associated with third risk level (e.g., a low risk level of coming into contact with a person infected with COVID-19). It is noted that while the illustrative example above is described as including a density parameter that includes an array having three different values, the density parameter array may include more than three or less than three values depending on the number of different cluster densities desired for a particular use case. In some embodiments, at least two values may be included in the density parameter array.

The set of parameters may include a size parameter that specifies a metric associated with cluster size, such as a metric that specifies a radius (r) of a cluster. In an aspect, the size parameter may be specified as an input array with different size of clusters. It is noted that while aspects of the present disclosure are described with reference to a radius metric being used as the size parameter, other types of metrics may be used and such other metrics may require modification of the radius-based processes described herein. Further, it is noted that while the size parameter may be specified as a radius metric, such disclosure should not be understood to require that clusters must be circular—indeed, embodiments of the present disclosure may identify clusters having non-circular shapes, as described herein.

The set of parameters may also include a node parameter set that specifies node information. In an aspect, the node information included in the node parameter set may be an array of location information associated with a plurality of nodes. Each node of the plurality of nodes may be identified in the array using a location within a coordinate system. In an aspect, the coordinate system may be a real-world coordinate system and the location of each node of the plurality of nodes may be specified using latitude (p) and longitude (q) coordinate pairs. To illustrate, suppose the plurality of nodes includes three nodes: $node_1$ ($n_1$), $node_2$ ($n_2$), $node_3$ ($n_3$). Node $n_1$ may have a location $[p_1, q_1]$, node $n_2$ may have a location $[p_2, q_2]$, and node $n_3$ may have a location $[p_3, q_3]$. It is noted that while the example above describes the location information as being specified using latitude and longitude, in some aspects other techniques for specifying locations may be used, such as virtual coordinate systems. The node information may be utilized to determine distances between nodes, which may be utilized to identify clusters according to the concepts described herein. Additional aspects of the functionality provided by the clustering engine 120 and the use cases that may be supported by the operations of the clustering engine 120 are described in more detail below.

As shown in FIG. 1, the one or more user devices 130 may include one or more processors 132, a memory 134, and one or more I/O devices 138. The one or more processors 132 may include one or more microcontrollers, ASICs, FPGAs, CPUs and/or GPUs having one or more processing cores, or other circuitry and logic configured to facilitate the operations of the user device(s) 130 in accordance with aspects of the present disclosure. The memory 134 may include RAM devices, ROM devices, EPROM, EEPROM, one or more HDDs, one or more SSDs, flash memory devices, NAS devices, or other memory devices configured to store data in a persistent or non-persistent state. Software configured to facilitate operations and functionality of the one or more user devices 130 may be stored in the memory 134 as instructions 136 that, when executed by the one or more processors 132, cause the one or more processors 132 to perform the operations described herein with respect to the user devices 130. The one or more I/O devices 138 may include one or more display devices, a keyboard, a stylus, one or more touchscreens, a mouse, a trackpad, a camera, one or more speakers, haptic feedback devices, a global positioning system (GPS) or other location tracking functionality, or other types of devices that enable the user device to receive information from and/or provide information to the clustering device 110.

The data sources 160, 170, 180 may include closed circuit television (CCTV) camera feeds, satellite camera feeds, global positioning system (GPS) data sources, government agencies, healthcare organizations, vehicles, network infrastructure (e.g., cellular base stations, access points, etc.), or other types of data sources that may provide node information to the clustering device 110, as described in more detail below. It is noted that the one or more user devices 130 may also be configured to provide node information to the clustering device 110. For example, the node information provided by the user device(s) 130 may include information identifying each node (e.g., each user device 130) and location data of each node. The location data may include GPS data, location data derived via triangulation (e.g., based on known locations of base stations or other network infrastructure serving the user device(s)), or other types of location data (e.g., locations detected via scans of near field communication (NFC) or other devices using the user devices 130, etc.). Exemplary use cases where the above-described sources of node information may be leveraged by the clustering device 110 according to aspects of the present disclosure are described in more detail below.

As briefly described above, the clustering device 110 may utilize the set of parameters to identify clusters having varying densities. The set of parameters and the sources from which the set of parameters are derived may vary according to the particular use case being supported by the clustering device 110. The size parameter may be configured by an administrator responsible for managing an application providing user-facing functionality for the particular use case and may be configured based upon the specific use case. For example, a use case supporting COVID-19 hot spot monitoring may utilize a first size parameter, a traffic monitoring use case may utilize a second size parameter, and a use case supporting a weather application may utilize a third size parameter. It is noted that while different size parameters for different use cases may be common, it is not a requirement and different use cases may utilize clustering algorithms of the present disclosure having the same size parameter if desired. Accordingly, it is to be understood that the size parameter may be different between some use case for which the clustering algorithms of the present disclosure may be utilized and may be the same for other use cases.

Additionally, the density parameter may be configured according to the particular use case to which the disclosed clustering algorithm is applied and different use cases may use the same or different numbers of density values (e.g., the minPts[ ] array may have 2 density values for some use cases, 3 density values for other use cases, and more than three density values for other different use cases). Thus, it is to be understood that the density parameter may be configured to specify different density values and different quantities of density values (e.g., larger or smaller minPts[ ] arrays) depending on the needs of a particular use case to which the disclosed clustering algorithm is applied.

Figure 2:
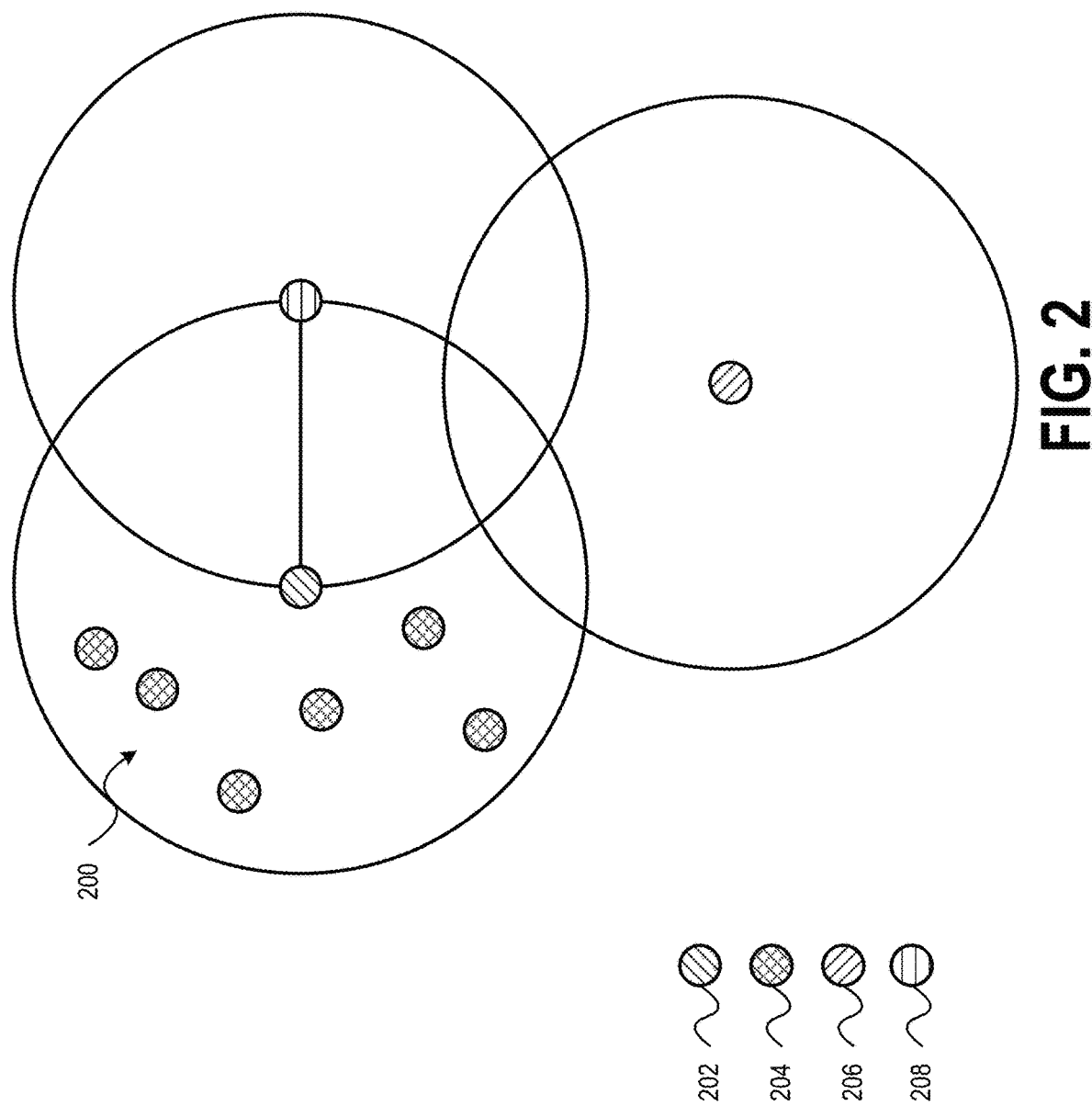
FIG. 2 is block diagram illustrating additional aspects of identifying clusters in accordance with embodiments of the present disclosure.

The clustering algorithm utilized by the clustering engine 120 may identify clusters based on different point types. The different point types may include core points, border points, and noise points. A core point may correspond to a particular point which is within a neighborhood determined based on the size parameter (e.g., the radius) that has a greater value than a precise number of points that is minPts[i]. Border points may be particular points which have a Euclidian distance (Eps) within the neighborhood having less value than a precise number of points that is minPts[i]. Noise points may be points that do not fall under the core or border point. Referring briefly to FIG. 2, a block diagram illustrating aspects of point types utilized by clustering techniques of embodiments is shown. In FIG. 2, a cluster 200 is shown and includes a core point 202, a border point 208, density connected nodes 204, and a noise point 206. As can be appreciated from the illustration of FIG. 2, each of the density connected nodes 204 of the cluster 200 is within a size parameter r (e.g., the radius of the cluster 200). Additionally, noise point 206 is not density connected with the nodes 208 and therefore does not fall within the cluster 200.

Referring back to FIG. 1, upon receiving the set of parameters, the clustering engine 120 may utilize the node information (e.g., the location information for each node) to obtain coordinate information for each node. In the coordinate system, each location may be specified as a pair of values (x, y), which may represent the latitude (p) and longitude (q) described above. The clustering engine 120 may select a node $p_1$ from the node array ($p_n$). The clustering algorithm may then determine all nodes that are reachable from the node $p_1$ with respect to the radius (e.g., the size parameter). In an aspect, nodes may be determined to be reachable from the node $p_1$ based on a Euclidean distance calculated between the node $p_1$ and the selected node. The Euclidean distance formula may be expressed as:

$$d(p,q) = \sqrt{(q_1-p_1)^2 + (q_2-p_2)^2}, \quad \text{(Equation 1)}$$

where d is the Euclidian distance between points p and q, p is the selected node, q is the node being evaluated to determine whether it is reachable from the node p, ($p_1$, $q_1$) represents the coordinates of node p, and ($p_2$, $q_2$) represents the coordinates of node p. Nodes that are reachable from the selected node p may be determined to be density connected and assigned to a temporary cluster Tc[ ].

Stated another way, the clustering engine 120 may assign all nodes whose distance with other nodes is greater than radius r to temporary cluster Tc[ ].

$$\forall k \in (0 \ldots NL) TC_k = \forall j \in (0 \ldots NL) \begin{cases} N_j & d(N_1, N_j) \leq r \\ 0 & d(N_1, N_j) > r \end{cases}, \quad \text{(Equation 2)}$$

where NL is the Node size, r is the radius (e.g., the size parameter), $d(N_1, N_j)$ is the distance. If the clustering engine 120 determines that a current node is a core node, a cluster may be formed or identified. If the selected node p is a border point, the clustering engine 120 may determine that there are no nodes that are density reachable from the node and may proceed repeat the above-described process with a next node $p_2$.

The clustering engine 120 may determine whether a density of the temporary cluster Tc[ ] is greater than minPts [i]. It is noted that because minPts[ ] can include multiple densities, as described above, multiple temporary clusters Tc[ ] associated with different densities may be generated (and used to construct confirmed clusters Cr), each temporary cluster being based on a density specified in the density parameter (e.g., the minPts[ ] array). This allows the clustering engine 120 to identify clusters having different densities without requiring multiple executions of the clustering algorithm using different density parameters. By avoiding multiple executions of the clustering algorithm, the invention conserves computing and/or memory resources as compared to conventional techniques and solutions. If the density of a temporary cluster Tc[ ] is greater than minPts[i], the temporary cluster Tc[ ] may add the node to a confirmed cluster Cr[minPts[i]], where i is an index ranging from 0 to the size of minPts[ ]. The process for evaluating the density of the temporary cluster Tc[ ] may expressed as:

$$Cr_n = \{TC_k k > \text{minPts}_n, n \in (1 \ldots ml), \quad \text{(Equation 3)}$$

where ml is the size of minPts[ ] array. The processes described above with reference to Equations 1-3 may continue until all the nodes are processed.

Figure 3:
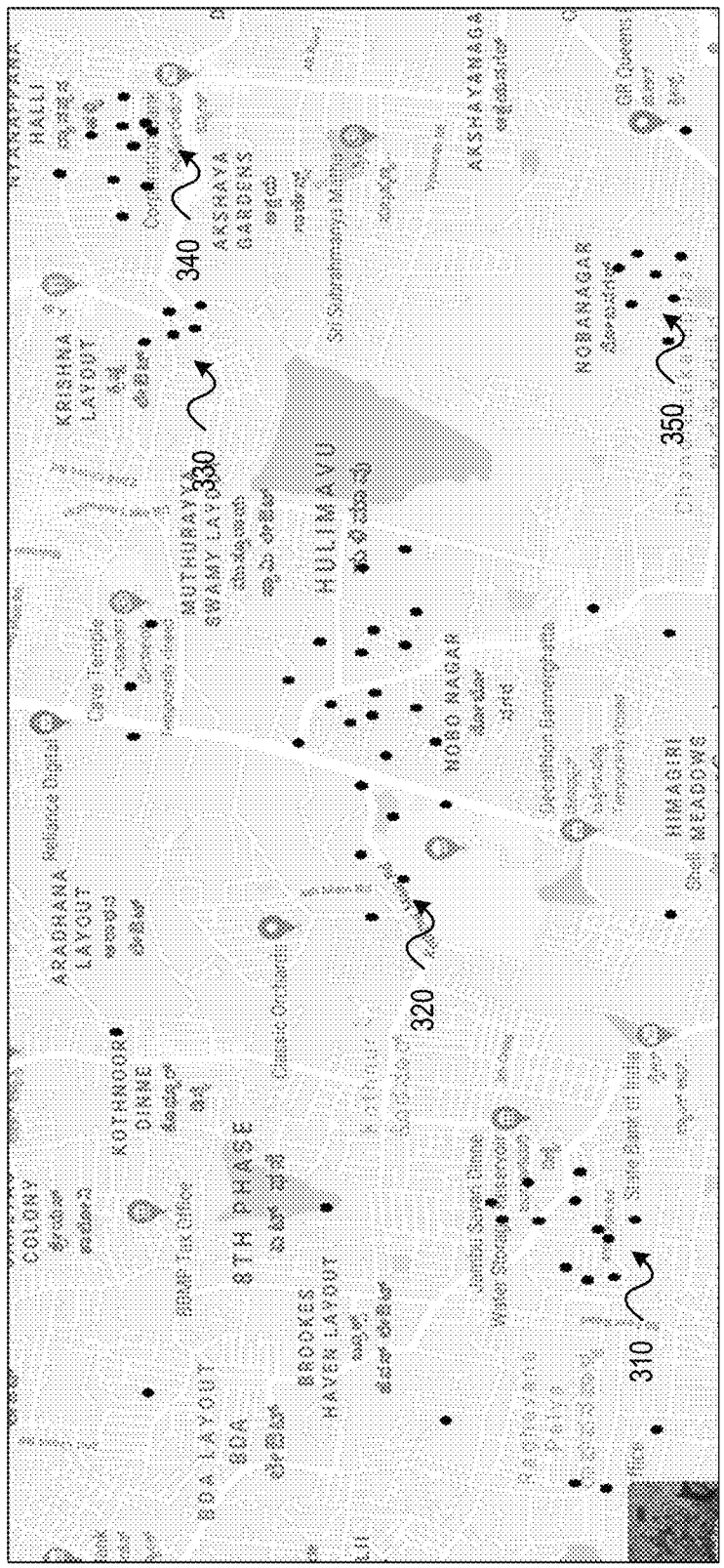
FIG. 3 is a screenshot of a data set that may be analyzed using clustering algorithms in accordance with embodiments of the present disclosure.

As shown above, the DENSVAR algorithms of embodiments may find distances across all nodes or data points (e.g., using Equation 1) and then categorize the nodes or data points to one or more temporary clusters based on an input array of densities (e.g., minPts[ ]), each different temporary cluster of the one or more temporary clusters corresponding to a different density level. The temporary clusters may be configured as a two-dimensional temporary cluster array with different densities as rows in a matrix. The density varying clustering algorithm described above may enable the clustering engine 120 to provide functionality that supports various applications to which the concepts of the present disclosure may be applied. To illustrate, an application may be provided to the user device(s) 130 to display a map of hot spots related to an infectious disease, such as COVID-19. In an aspect, the map may be the map shown in FIGS. 3 and 4, which are screenshots of a map utilized to demonstrate certain illustrative concepts of the present disclosure. The clustering device 110 may be configured to receive input data 190 that may be used to identify clusters representing different densities of persons having COVID-19, thereby enabling health personnel or individuals to identify areas where there are many infected persons (e.g., identify "hot spots") and avoid those areas or detect areas where certain safety measures (e.g., masks, social distancing practices, etc.) should be implemented. In this exemplary use case, the input data 190 may include location information that identifies locations of individuals infected with COVID-19, which may be obtained from a data source, such as one or more hospitals, a government agency (e.g., the Center for Disease Control (CDC), etc.).

Figure 4:
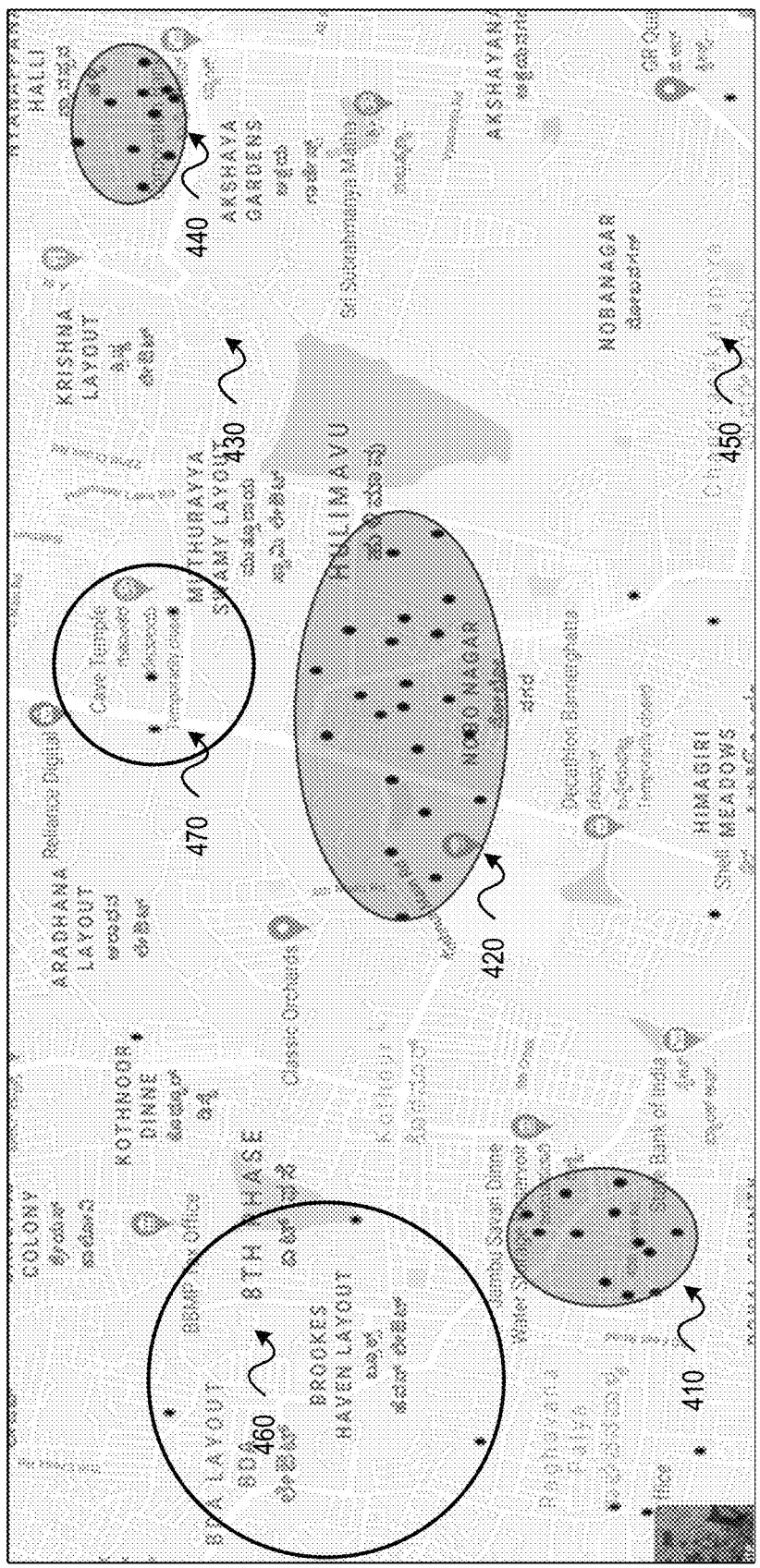
FIG. 4 is an image or screenshot illustrating identification of clusters of varying densities according to aspects of the present disclosure.

As described above with respect to the set of parameters utilized by the clustering engine 120, the location information included in the input data 190 may provide the node information. In this example use case, the node information may reflect a population of persons that have tested positive for COVID-19. To illustrate and referring to FIG. 3, a screenshot of a data set that may be analyzed using DENSVAR clustering algorithms in accordance with aspects of the present disclosure. The data set illustrated in FIG. 3 may represent a population of individuals that have tested positive for an infectious disease (e.g., COVID-19), and each person may represent a node within the node information. The population of individuals includes sub-populations 310, 320, 330, 340, 350, each comprising a set of nodes or individuals that makes up a subset of the population of individuals. Results from processing each of these nodes using the above-described techniques are shown in FIG. 4, which illustrates 5 different clusters that were identified. The 5 different clusters that were identified includes a first cluster 410, a second cluster 420, a third cluster 430, a fourth cluster 440, and a fifth cluster 450, and each of the clusters 410, 420, 430, 440, 450 may include a subset or sub-population of the entire population (e.g., each sub-population or cluster may include multiple nodes or individuals). It is noted that the nodes present within the solid circles 460, 470 may be considered by the clustering engine 120, but may not have been included in any of the clusters because no core point was found or those nodes were not density connected to other nodes with the identified hot spots represented by clusters 410, 420, 430, 440, 450. It is also noted that the clusters 410, 420, 430, 440, 450 include different densities (e.g., cluster 410, 420, 440 may have similar density while clusters 430, 450 may have different densities compared to the densities of 410, 420, 440).

The ability to rapidly identify clusters of individuals having an infectious disease may provide various new capabilities that may be used to mitigate the spread of such diseases and also to contain them. For example, a government agency may provide the clustering device 110 with the appropriate information (e.g., at least a portion of the set of parameters used by the clustering engine 120) that includes the locations of the sub-populations 310, 320, 330, 340, 350 and the clustering device 110 may output cluster data 126 that, in this example use case, may represent COVID-19 hot spots as regions on a map, as shown in FIG. 4. Moreover, the regions may be associated with different densities, which may enable the different regions to be labeled with a risk level. For example, the regions corresponding to clusters 410, 420, 440 may have a higher density than the regions corresponding to clusters 430, 450. The outputs of the clustering engine 210 may be configured to enable presentation of the clusters 410, 420, 440 as regions having a first risk level (e.g., a high risk level) and presentation of the clusters 430, 450 as regions having a second risk level (e.g., a moderate risk level). In this example, the second risk level may be lower than the first risk level due to the lower density of COVID-19 infections in the geographic regions corresponding to the clusters 430, 450 as compared to the clusters 410, 420, 440. In an aspect, the cluster data 126 may be transmitted to the user device 130 where it may be used by an application running on the user device to display the COVID-19 hot spots. It is noted that implementation of the concepts shown in FIGS. 3 and 4 may not result in actual distribution of information to user devices that identify the actual and specific locations of individuals that are infected with COVID-19 (e.g., due to privacy concerns and regulatory requirements) and instead may distribute information representing geographic areas corresponding to the different identified clusters. Different types of shading, coloring, line patterns, etc. may be used to indicate different densities of the cluster regions and present the cluster data 126 to the users of the user devices 130. Providing such information may enable users of the user devices 130 to make informed decisions on where infectious diseases, such as COVID-19, are present and the risk levels (e.g., likelihood of encountering someone that has the infectious disease) associated with such areas.

The ability to identify clusters may enable health care professionals to identify trends in the spread of infectious diseases, monitor the status of safety measures placed to mitigate the spread of the infectious diseases, and other use cases. As an example of an additional use case to which the above-described functionality may be extended, social distancing compliance has recently become a topic of interest due to the spread of COVID-19. The clustering device 110 may be utilized to facilitate monitoring of social distancing practices by identifying clusters of individuals that are not maintaining acceptable levels of social distancing and may alert various individuals or officials when social distancing practices are not being observed.

Figure 5:
FIG. 5 is a screenshot of a camera feed that may be analyzed using clustering algorithms and clustering devices in accordance with aspects of the present disclosure.

In such a use case, the clustering device 110 may receive data feeds (e.g., as the input data 190) from various ones of the data sources 160, 170, 180, which may include closed circuit television (CCTV) data feeds. The data feeds may be received from public spaces (e.g., subway stations, airports, parks or beaches, train stations, or other high traffic public areas, such as camera feeds in Times Square, etc.) or from private spaces (e.g., office buildings, stadiums, college buildings or classrooms, bars, etc.). The clustering device 110 may be configured to analyze the data feeds received as input data 190 using the techniques described above in order to identify clusters and determine whether social distancing practices are being followed. It is noted that since the input data 190 in this case is CCTV camera feeds, additional processing may be performed in order to obtain portions of the data utilized by the clustering engine 120. An exemplary screenshot of a CCTV camera feed that may be analyzed by the clustering device 110 in accordance with aspects of the present disclosure is shown in FIG. 5.

Unlike the use case and examples described previously, the use cases involving analysis of CCTV camera feeds may require the clustering device 110 to derive the location data associated with the nodes. To support such use cases, the clustering device 110 may be configured with image processing and recognition functionality that enables the clustering device 110 (e.g., the clustering engine 120 or another module or component of the clustering device) to determine node and location information from the CCTV data feeds.

The image processing and recognition functionality utilized to analyze CCTV or other video data feeds may include object detection, classification functionality, and depth analysis functionality. The object detection and classification functionality may utilize machine learning techniques to identify persons present within the area viewed by the camera feed(s). The machine learning techniques may utilize a convolutional neural network to identify individuals present within the field of view, such as to detect facial features of persons present within the field of view or other information (e.g., hats, glasses, etc.) that may enable the clustering engine 120 to identify nodes (e.g., individuals) present with the camera feed(s).

Once the object detection and classification is complete, the clustering engine 120 may determine the depth of the identified objects (e.g., the nodes or individuals present in the feed(s)). In an aspect, the depth of the identified objects may be determined using a triangle similarity technique, which may be expressed by the following:

$$F=(P\times D)/H, \qquad \text{(Equation 4)}$$

$$D'=(H\times F)/P, \qquad \text{(Equation 5)}$$

where F represents the focal length of the camera(s), p represents the pixel height of a person, d represents the distance of an identified object from the camera, and h represents the actual height of a person. The depth of the identified objects may be used to calculate a Euclidean distance between all identified objects, which allows the camera feeds to be used to generate clusters of varying densities using the above-described techniques. It is noted that in aspects where the concepts disclosed herein are utilized for monitoring social distancing practices or other applications to which the concepts described herein may be applied the size parameter may be configured to a smaller distance than in other use cases or applications. For example, in the example above where COVID-19 hot spots are identified, the size parameter (e.g., the radius parameter) may be specified in terms of 10s of meters (e.g., 20, 30, 40, 50, 60, 70, 80, 90 meters), hundreds of meters (e.g., 100, 200, 300, 400, 500, 600, 700, 800, 900 meters), kilometers (e.g., 1, 5, 10, 20, . . . , 100 km or greater), or another unit of measure. In contrast, use cases such as social distance monitoring may utilize smaller size parameters. For example, social distancing practices suggest individuals maintain at least 2 meters of separation to minimize the chances of spreading COVID-19, which may cause the clustering engine 120 to utilize a size parameter in the sub-10 meter range. However, it is noted that in some configurations a social distancing use case (or other type of use case) may utilize larger size parameters (e.g., a size parameter in the 10s of meters range).

Based on density clustering analysis by the clustering engine 120, the clustering device 110 may determine whether any clusters are identified based on the input data 190 (e.g., the camera feeds) where social distancing practices are not being followed. If any clusters are identified as not following social distancing practices, the clustering device 110 may generate one or more notifications that may be transmitted to one or more entities. For example, where the input data 190 is related a public area the notification may be transmitted to public servants (e.g., police, firemen, etc.) or other entities responsible for maintaining the safety of the public area. Where the input data 190 is received from a private organization, the notification(s) may be transmitted to an owner or other entity responsible for managing the area depicted in the input data 190, such as a manager, a third-party security service, etc. In some aspects, notifications may be transmitted to multiple entities when clusters indicating social distancing practices are not being followed are detected by the clustering device 110. For example, if input data indicates social distancing practices are not being observed at a public beach, a notification may be transmitted to a government agency or department responsible for managing the beach (e.g., a parks and wildlife department, etc.) and the police. In an aspect, the notification may indicate the location where the cluster was identified, a density of the cluster, or other information.

The one or more databases 118 stored at the memory 114 of the clustering device 110 may include a contact database that specifies contact information for transmitting notifications based on characteristics of observed clusters. For example, each CCTV camera feed may be associated with a specific location and the contact database may include contact information that associates each camera feed with a particular contact or set of contacts, where each contact has at least one form of contact information associated therewith (e.g., e-mail, telephone number, and the like). The contact database may be used to determine which entities or individuals should be contacted when a cluster having a density that exceeds a threshold is identified, such as to specify e-mail addresses, telephone numbers, etc. that should be used to transmit the notification. In an aspect, the notification may be transmitted via multiple communication channels, such as an e-mail, a text message, an automated voice response message, or other type of communication channel. Using the aforementioned social distance monitoring techniques may enable real-time or near real-time (e.g., subject to processing of the data feeds using the techniques described herein) of social distancing practices and notification of appropriate persons when social distancing is not being followed, which may help reduce the spread of certain infectious diseases, such as COVID-19.

Figure 6:
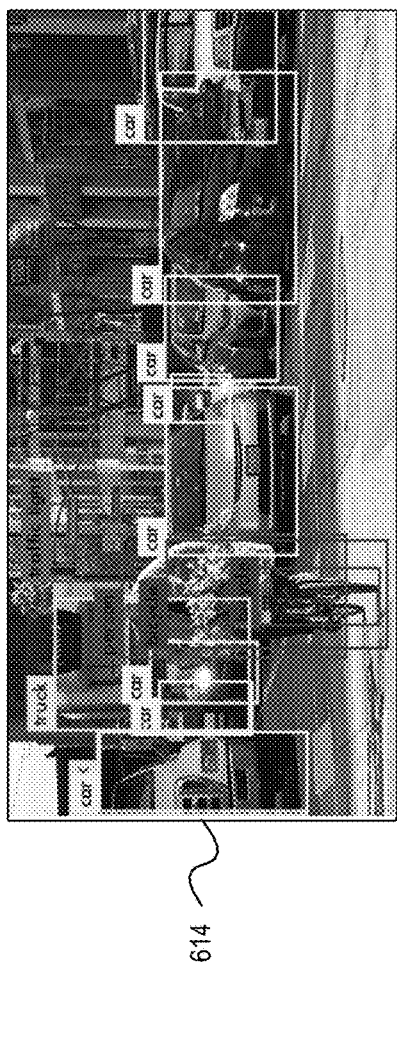
FIG. 6 is a diagram illustrating performing traffic monitoring using clustering algorithms in accordance with aspects of the present disclosure.

It is noted that while the above-described use cases have been described primarily with reference to monitoring characteristics related to contagious diseases, embodiments of the present disclosure are not limited to such use cases. For example, and referring to FIG. 6, a diagram illustrating application of the clustering techniques described herein to monitor traffic congestion is shown. As illustrated in FIG. 6, cameras 610, 620 may be disposed proximate a street such that the cameras 610, 620 have viewing that enable traffic (e.g., vehicles travelling on the street) to be viewed. In FIG. 6, the camera 610 has a viewing angle facing the direction indicated by arrow 612 and the camera 620 has a viewing angle facing the direction indicated by arrow 622. Image 614 illustrates an exemplary image that may be present in a camera feed provided by the camera 610 (or the camera 620). Using the image and video analysis techniques described above with reference to FIG. 5, the camera feed may be provided as the input data 190 of FIG. 1 to the clustering device 110 and analyzed to identify clusters representative of different densities of traffic present on a road system.

The cluster data (e.g., the cluster data 126 of FIG. 1) generated based on monitoring the camera feeds may be provided to the user devices 130 to indicate the density of traffic at various portions of a road system. For example, the user devices 130 may include an application (e.g., a traffic monitoring or navigation application) that displays information representative of traffic present on the road. In aspects, the cluster data may identify different levels of traffic (e.g., different traffic density levels), which may be color coded for display on the application. To illustrate, heavy traffic may be indicated as red, moderate traffic may be indicated as yellow, and light or no traffic may be indicated as green. One advantage that may be realized through the use of the clustering techniques of the present disclosure to provide traffic monitoring functionality is the speed at which clustering techniques may be performed. For example, because the techniques disclosed herein enable multiple density clusters to be identified in a single run, multiple traffic densities can be identified more quickly, enabling the application to provide real-time or near real-time visibility into live traffic congestion on a road system. In contrast, conventional techniques may require multiple runs to identify multiple density clusters, which is computationally inefficient (e.g., consumes more power, takes more time, requires more processor and memory utilization, etc.). It is noted that while FIG. 6 illustrates two traffic cameras, it is to be understood that more than two cameras may be utilized to provide updates to a traffic application. Moreover, due to the more efficient processing of input data provided by the clustering techniques described herein, larger volumes of traffic camera data may be processed in less time than previously available clustering algorithms, such as DBSCAN and HDBSCAN techniques that have difficulty working with large data sets. For example, analyzing a large database using existing clustering algorithms, such as DBSCAN and HDBSCAN may increase computational complexity by a factor of N as compared to the DENSVAR algorithms described herein. The reduced computational complexity realized by the DENSVAR algorithms of embodiments may realize reduced computational complexity and faster execution times due, at least in part, to the ability to simultaneously consider a number of layers/levels of clusters (e.g., different density levels, cluster sizes, etc.)

in a single run of execution, allowing more efficient analysis of datasets maintained in large databases.

It is also noted that while the traffic monitoring use case described above utilizes traffic camera data as the input to the clustering engine 120, embodiments providing functionality for supporting traffic monitoring applications are not limited to camera data feeds. For example, user devices (e.g., the user devices 130 of FIG. 1) may provide location data to the clustering device 110 (e.g., as the input data 190) and the location data may be utilized to detect the presence of traffic on roadways. In some aspects, utilization of location data provided by user devices may be processed to detect whether the user device is travelling at a rate of speed that is indicative of the user(s) driving a vehicle rather than walking adjacent to the road(s). In some aspects, some of the user devices providing location data to the clustering device 110 may include information with the location data that indicates whether the user is driving (e.g., the user device 130 may determine whether the user is driving instead of the clustering device 110). Thus, it is to be understood that the clustering device 110 may utilize different types of input data to provide traffic monitoring functionality according to the concepts described herein.

In some aspects, the density clusters identified for traffic conditions may also be used by the traffic monitoring application to optimize navigation of a vehicle. For example, a navigation system may be provided with the cluster data and the navigation system may utilize the cluster data to identify high density traffic clusters on various available routes from a first location (e.g., a point of origin or current location) to a destination. The navigation application may then configure the suggested path of travel such that a shortest path between the first location and the destination that is optimized to avoid high traffic density areas is presented to the user. In an aspect, Dijkstra's algorithm may be used to optimize the path of travel.

The traffic monitoring concepts described above may also be used to non-motorized travel. For example, many locations experience heavy foot traffic, such as theme parks or other public destinations (e.g., Times Square in New York, malls, etc.). Some of these locations provide applications that enable users to view maps of the location, such as a theme park application providing a map of the theme park to help visitors navigate to the various attractions of the theme park. Such applications may utilize GPS or other location functionality of the user devices they reside on to provide location data to the clustering device 110 and the location data may be used to detect clusters representative of different foot traffic densities, which may be displayed in the map provided by the application and used to optimize paths of travel between different attractions or destinations. Accordingly, it is to be understood that traffic monitoring use cases to which the clustering techniques described herein may be applied are not limited to motorized traffic.

Another exemplary use case to which the clustering techniques described herein may be applied is consumer demand for goods. E-commerce platforms receive orders for goods from geographically disparate consumers and then ship the ordered goods to the consumers from one or more distribution centers. The concepts described herein may be utilized to develop density clusters representative of demand for good from different geographic regions. To determine the cluster data, the e-commerce providers may provide information associated with historical orders to the clustering device 110 and the clustering device 110 may analyze the locations where orders for particular products were shipped using the clustering techniques described herein to develop demand profiles for the different products. The demand profiles may correspond to density clusters identifying demand for different products across disparate geographic regions. The cluster data may then be provided to the e-commerce providers where it may be used to optimize marketing efforts (e.g., emphasize marketing efforts where demand is high to maintain consumer demand or emphasize marketing efforts in areas where demand is low to increase consumer demand), optimize order fulfillment (e.g., stock fulfillment centers in geographic areas where products have high demand more frequently or with higher quantity on hand as compared to fulfillment centers in geographic areas where consumer demand is low), or for other purposes. The concepts described above may also be utilized for non-e-commerce applications as well.

The concepts described herein may also be applied to various weather use cases. For example, weather data (e.g., temperature, precipitation, wind, etc.) for various geographic locations may be provided (e.g., as the input data 190) to the clustering device 110. The temperature or weather data may be generated by various sensors and each sensor may be associated with a particular geographic location. The clustering engine 120 may analyze the weather data to generate clusters that may be used to identify weather conditions at one or more locations. The weather condition clusters may be presented to users via a geographic map or other graphical user interface. For example, when travelers enter a city or country, an application configured to utilize the DENSVAR algorithms described herein may present a map that shows which regions have different density levels of temperature from high to low. The users may then plan travel based on the different levels of temperature illustrated by the displayed clusters. Similar to some of the use cases described above, the weather density clusters may be used to display information to a user (e.g., via the user device 130). For example, a map showing the weather density clusters may be presented and different colors may be used to represent different weather features related to each cluster (e.g., one color for a cluster associated with clear weather, a different color for clusters related to storms, another color to represent cloudy weather, and so on).

As yet another example of the use cases to which the concepts described herein may be applied, the cluster data generated by the clustering device 110 may be utilized to optimize communication networks. For example, base stations of one or more communication networks (e.g., evolved nodeBs (eNBs), next generation nodeBs (gNbs), femtocells, picocells, or other types of access points providing communication functionality) may provide data to the clustering device 110 associated with network traffic and bandwidth utilization. The input data received from the base stations may be used to generate density clusters representative of demand for bandwidth and communication services within the communication network(s). Such information may enable network access service providers to identify regions or areas within the communication network where additional bandwidth or capacity may be needed (e.g., to serve high density traffic clusters where network bandwidth experiences high demand) or other optimizations. The network traffic and utilization of different base stations (as represented by different density clusters, may be utilized to categorize locations into different levels of clusters to increase communication bandwidth provided by the base station of the network, such as to identify locations where additional base stations should be deployed to relieve network congestion or other network optimizations. It is noted that the DENSVAR algorithms described above may also be used to predict demand for even a single base station, rather than requiring the algorithm to be applied to multiple base stations. For example, the DENSVAR algorithm may be applied to a dataset that represents historic demand for the base station over time and may be used to identify clusters of varying demand representative of demand over time for the base station, which may provide insights into times when the base station experience different density levels of demand.

As shown above, the density varying clustering algorithms disclosed herein enable arbitrary shaped clusters to be identified using a set of parameters (e.g., minPts[ ], size, and node parameters). Additionally, the clustering techniques of the present disclosure enable noise and outliers to be handled in a manner that improves the accuracy of identified clusters and corresponding accuracy improvements to the various use cases to which the identified clusters may be applied. Moreover, the disclosed clustering algorithms perform well with large differences in densities and require fewer executions to identify clusters of different densities as compared to previous clustering techniques, making the disclosed clustering techniques a more viable and practical solution for use cases where clusters of varying densities may be identified.

Figure 7:
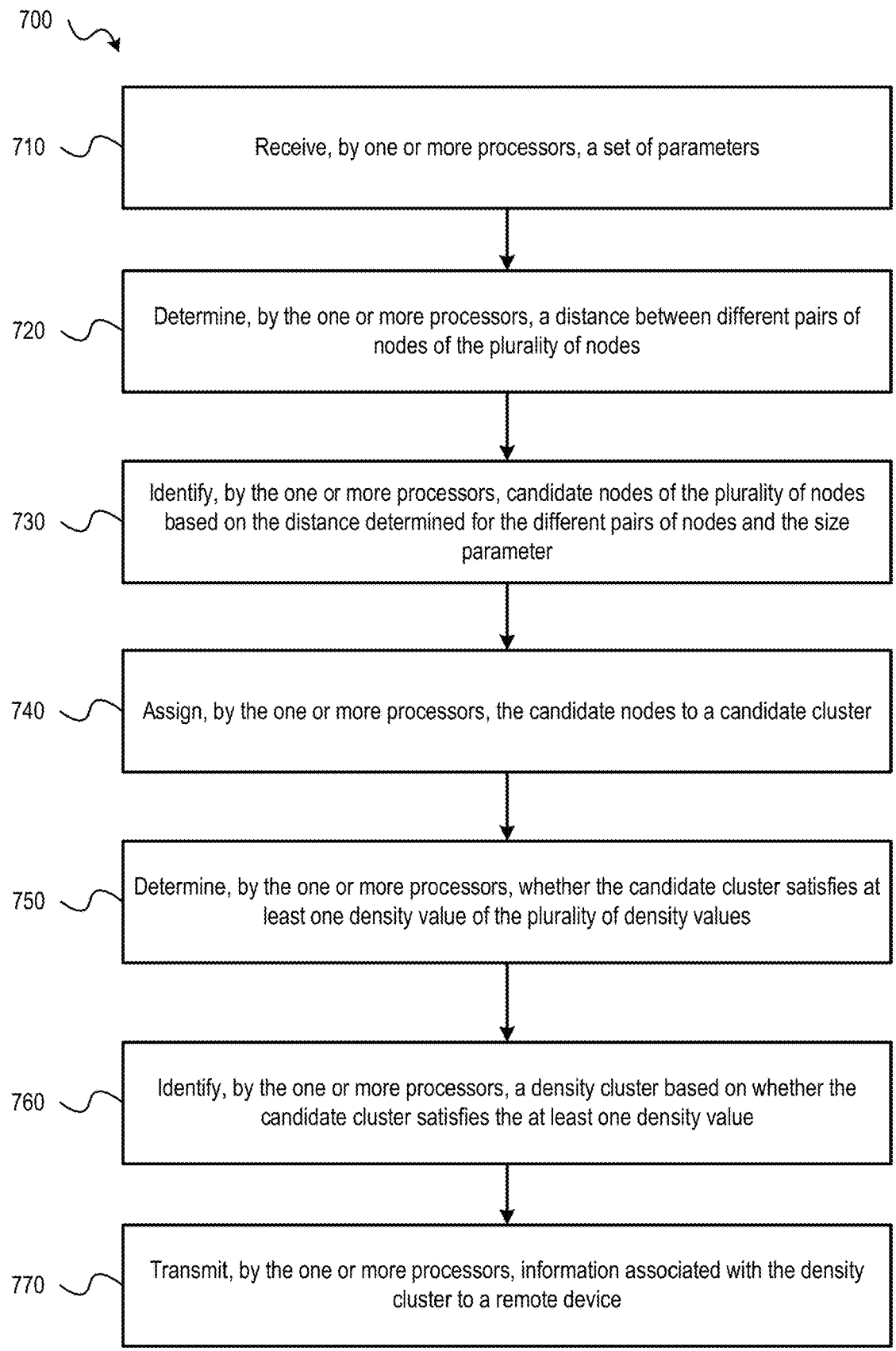
FIG. 7 is a flow diagram illustrating an exemplary method for leveraging identifying clusters having varying densities in accordance with aspects of the present disclosure.

Referring to FIG. 7, a flow diagram illustrating an exemplary method for leveraging identifying clusters having varying densities in accordance with embodiments of the present disclosure is shown as a method 700. In an aspect, the method 700 may be performed by a clustering device, such as the clustering device 110 of FIG. 1. Steps of the method 700 may be stored as instructions (e.g., the instructions 116 of FIG. 1) that, when executed by one or more processors (e.g., the one or more processors 112 of FIG. 1), cause the one or more processors to perform the steps of the method 700.

At step 710, the method 700 includes receiving, by one or more processors, a set of parameters. As described above with reference to FIG. 1, the set of parameters may include a density parameter, a size parameter, and a node parameter or node parameter set. At step 720, the method 700 may include determining, by the one or more processors, a distance between different pairs of nodes of the plurality of nodes. In an aspect, the distance may be a Euclidian distance, as described above with reference to FIG. 1. The distance may indicate how density connected the pair of nodes are and may take into consider whether the nodes are core nodes, border nodes, or noise nodes, as described with reference to FIG. 2. At step 730, the method 700 includes identifying, by the one or more processors, candidate nodes of the plurality of nodes based on the distance determined for the different pairs of nodes and the size parameter. As described above, the size parameter may indicate a radius (or other metric of distance) that may be used to provide a threshold indication of whether two nodes are density connected (e.g., if the distance between two nodes is less than the size parameter, they may be determined to be density connected).

At step 740, the method 700 includes assigning, by the one or more processors, the candidate nodes to a candidate cluster. As described above, nodes that are density connected to each other may be assigned to a candidate cluster, which is a temporary cluster of density connected nodes. At step 750, the method 700 includes determining, by the one or more processors, whether the candidate cluster satisfies at least one density value of the plurality of density values. As described above, the density parameter may include an array (minPts[ ]) that specifies a plurality of density values (e.g., a high density value, a moderate density value, and a minimum density value). At step 760, the method 700 includes identifying, by the one or more processors, a density cluster based on whether the candidate cluster satisfies the at least one density value. A candidate cluster formed of nodes that are sufficiently density connected to satisfy at least one of the densities identified in the density parameter may be identified as a cluster by the clustering algorithm. It is noted that candidate clusters that do not satisfy at least one of the density parameter values may be deemed insufficiently dense to be identified as a cluster and may be ignored (e.g., as illustrated in FIG. 4 where certain sparsely distributed nodes illustrated in the drawing are not identified as belonging to the clusters 410-450).

At step 770, the method 700 includes transmitting, by the one or more processors, information associated with the density cluster to a remote device. In aspects, the information associated with the density cluster may be a notification (e.g., a notification that social distancing practices are not being followed or some other characteristic derived from the identified density cluster). In some aspect, the information associated with the density cluster may include information for presentation at a user interface of a user device, such as information to display the identified cluster or clusters within a map or application of a user device (e.g., the user device 130 of FIG. 1), as described above. In some aspect, the method 700 may identify additional clusters including clusters having different densities than the density cluster identified in step 760.

The method 700 may be readily applied to a variety of use cases, such as to display information associated with the density of persons affected by an infectious disease within a map, determine whether social distancing practices are being followed, monitoring traffic (e.g., foot traffic, vehicle traffic, air traffic, etc.), analyzing consumer demand for one or more products, and analyzing communication network demand. It is noted that these exemplary use cases are provided for purposes of illustration, rather than by way of limitation and that clustering algorithms of embodiments may be readily applied to additional use cases other than those specifically described herein.

Those of skill in the art would understand that information and signals may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

The functional blocks and modules described herein (e.g., the functional blocks and modules in FIGS. 1-7) may comprise processors, electronics devices, hardware devices, electronics components, logical circuits, memories, software codes, firmware codes, etc., or any combination thereof. In addition, features discussed herein relating to FIGS. 1-75 may be implemented via specialized processor circuitry, via executable instructions, and/or combinations thereof.

As used herein, various terminology is for the purpose of describing particular implementations only and is not intended to be limiting of implementations. For example, as used herein, an ordinal term (e.g., "first," "second," "third," etc.) used to modify an element, such as a structure, a component, an operation, etc., does not by itself indicate any priority or order of the element with respect to another element, but rather merely distinguishes the element from another element having a same name (but for use of the ordinal term). The term "coupled" is defined as connected, although not necessarily directly, and not necessarily mechanically; two items that are "coupled" may be unitary with each other. The terms "a" and "an" are defined as one or more unless this disclosure explicitly requires otherwise. The term "substantially" is defined as largely but not necessarily wholly what is specified—and includes what is specified; e.g., substantially 90 degrees includes 90 degrees and substantially parallel includes parallel—as understood by a person of ordinary skill in the art. In any disclosed embodiment, the term "substantially" may be substituted with "within [a percentage] of" what is specified, where the percentage includes 0.1, 1, 5, and 10 percent; and the term "approximately" may be substituted with "within 10 percent of" what is specified. The phrase "and/or" means and or. To illustrate, A, B, and/or C includes: A alone, B alone, C alone, a combination of A and B, a combination of A and C, a combination of B and C, or a combination of A, B, and C. In other words, "and/or" operates as an inclusive or. Additionally, the phrase "A, B, C, or a combination thereof" or "A, B, C, or any combination thereof" includes: A alone, B alone, C alone, a combination of A and B, a combination of A and C, a combination of B and C, or a combination of A, B, and C.

The terms "comprise" and any form thereof such as "comprises" and "comprising," "have" and any form thereof such as "has" and "having," and "include" and any form thereof such as "includes" and "including" are open-ended linking verbs. As a result, an apparatus that "comprises," "has," or "includes" one or more elements possesses those one or more elements, but is not limited to possessing only those elements. Likewise, a method that "comprises," "has," or "includes" one or more steps possesses those one or more steps, but is not limited to possessing only those one or more steps.

Any implementation of any of the apparatuses, systems, and methods can consist of or consist essentially of—rather than comprise/include/have—any of the described steps, elements, and/or features. Thus, in any of the claims, the term "consisting of" or "consisting essentially of" can be substituted for any of the open-ended linking verbs recited above, in order to change the scope of a given claim from what it would otherwise be using the open-ended linking verb. Additionally, it will be understood that the term "wherein" may be used interchangeably with "where."

Further, a device or system that is configured in a certain way is configured in at least that way, but it can also be configured in other ways than those specifically described. Aspects of one example may be applied to other examples, even though not described or illustrated, unless expressly prohibited by this disclosure or the nature of a particular example.

Those of skill would further appreciate that the various illustrative logical blocks, modules, circuits, and algorithm steps (e.g., the logical blocks in FIGS. 6-7) described in connection with the disclosure herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present disclosure. Skilled artisans will also readily recognize that the order or combination of components, methods, or interactions that are described herein are merely examples and that the components, methods, or interactions of the various aspects of the present disclosure may be combined or performed in ways other than those illustrated and described herein.

The various illustrative logical blocks, modules, and circuits described in connection with the disclosure herein may be implemented or performed with a general-purpose processor, a digital signal processor (DSP), an ASIC), a field programmable gate array (FPGA) or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

The steps of a method or algorithm described in connection with the disclosure herein may be embodied directly in hardware, in a software module executed by a processor, or in a combination of the two. A software module may reside in RAM memory, flash memory, ROM memory, EPROM memory, EEPROM memory, registers, hard disk, a removable disk, a CD-ROM, or any other form of storage medium known in the art. An exemplary storage medium is coupled to the processor such that the processor can read information from, and write information to, the storage medium. In the alternative, the storage medium may be integral to the processor. The processor and the storage medium may reside in an ASIC. The ASIC may reside in a user terminal. In the alternative, the processor and the storage medium may reside as discrete components in a user terminal.

In one or more exemplary designs, the functions described may be implemented in hardware, software, firmware, or any combination thereof. If implemented in software, the functions may be stored on or transmitted over as one or more instructions or code on a computer-readable medium. Computer-readable media includes both computer storage media and communication media including any medium that facilitates transfer of a computer program from one place to another. Computer-readable storage media may be any available media that can be accessed by a general purpose or special purpose computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code means in the form of instructions or data structures and that can be accessed by a general-purpose or special-purpose computer, or a general-purpose or special-purpose processor. Also, a connection may be properly termed a computer-readable medium. For example, if the software is transmitted from a website, server, or other remote source using a coaxial cable, fiber optic cable, twisted pair, or digital subscriber line (DSL), then the coaxial cable, fiber optic cable, twisted pair, or DSL, are included in the definition of medium. Disk and disc, as used herein, includes compact disc (CD), laser disc, optical disc, digital versatile disc (DVD), hard disk, solid state disk, and blu-ray disc where disks usually reproduce data magnetically, while discs reproduce data optically with lasers. Combinations of the above should also be included within the scope of computer-readable media.

The above specification and examples provide a complete description of the structure and use of illustrative implementations. Although certain examples have been described above with a certain degree of particularity, or with reference to one or more individual examples, those skilled in the art could make numerous alterations to the disclosed implementations without departing from the scope of this invention. As such, the various illustrative implementations of the methods and systems are not intended to be limited to the particular forms disclosed. Rather, they include all modifications and alternatives falling within the scope of the claims, and examples other than the one shown may include some or all of the features of the depicted example. For example, elements may be omitted or combined as a unitary structure, and/or connections may be substituted. Further, where appropriate, aspects of any of the examples described above may be combined with aspects of any of the other examples described to form further examples having comparable or different properties and/or functions, and addressing the same or different problems. Similarly, it will be understood that the benefits and advantages described above may relate to one embodiment or may relate to several implementations.

The claims are not intended to include, and should not be interpreted to include, means plus- or step-plus-function limitations, unless such a limitation is explicitly recited in a given claim using the phrase(s) "means for" or "step for," respectively.

Although the aspects of the present disclosure and their advantages have been described in detail, it should be understood that various changes, substitutions and alterations can be made herein without departing from the spirit of the disclosure as defined by the appended claims. Moreover, the scope of the present application is not intended to be limited to the particular implementations of the process, machine, manufacture, composition of matter, means, methods and steps described in the specification. As one of ordinary skill in the art will readily appreciate from the present disclosure, processes, machines, manufacture, compositions of matter, means, methods, or steps, presently existing or later to be developed that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps.

What is claimed is:

1. A method comprising:
   receiving, by one or more processors, a set of parameters, the set of parameters comprising a density parameter, a size parameter, and a node parameter, wherein the density parameter comprises a plurality of density values that includes at least a first density value and a second density value, wherein the first density value and the second density value are different, and wherein the node parameter comprises information associated with a plurality of nodes;
   configuring, by the one or more processors, a first execution cycle of a density variation (DENSVAR) clustering algorithm based on the set of parameters;
   executing, by the one or more processors, the first execution cycle of the DENS VAR algorithm, wherein the first execution cycle comprises:
      determining a distance between different pairs of nodes of the plurality of nodes;
      identifying candidate nodes of the plurality of nodes based on the distance determined for the different pairs of nodes and the size parameter;
      assigning the candidate nodes to one of a plurality of candidate clusters;
      determining whether each candidate cluster of the plurality of candidate clusters satisfies at least the first density value or the second density value; and
      identifying a first density cluster based on a first candidate cluster of the plurality of candidate clusters satisfying the first density value and a second density cluster based on a second candidate cluster of the plurality of candidate clusters satisfying the second density value during the first execution cycle; and
   transmitting, by the one or more processors, information associated with the first density cluster and the second density cluster to a remote device.

2. The method of claim 1, wherein determining the distance between the different pairs of nodes of the plurality of nodes comprises:
   selecting a first node of the plurality of nodes and a second node of the plurality of nodes; and
   determining a distance between the first node and the second node, wherein the distance between the first node and the second node indicates whether the second node is reachable from the first node.

3. The method of claim 1, a first node is identified as one of the candidate nodes when the first node is reachable from a second node based on the size parameter.

4. The method of claim 1, further comprising identifying additional density clusters based on whether additional candidate clusters satisfy at least one of the plurality of density values.

5. The method of claim 1, wherein the plurality of candidate clusters include clusters having different densities.

6. The method of claim 1, further comprising:
   compiling cluster data based on identified density clusters, the cluster data comprising information associated with one or more characteristics of nodes included in the first and second density clusters; and
   outputting the cluster data to a display device.

7. The method of claim 6, wherein the information associated with the one or more characteristics comprises information representative of at least one characteristic selected from the list consisting of: a density of persons affected by an infectious disease within a geographic region corresponding to the first density cluster or the second density cluster; an indication of whether social distancing practices are being followed within the geographic region corresponding to the first density cluster or the second density cluster; traffic density within the geographic region corresponding to the first density cluster or the second density cluster; consumer demand for one or more products within the geographic region corresponding to the first density cluster or the second density cluster; and communication network demand within the geographic region corresponding to the first density cluster or the second density cluster.

8. The method of claim 1, wherein the information associated with the first density cluster and the second density cluster comprises a notification and is transmitted to a user device of an entity associated with a geographic region corresponding to the first density cluster or the second density cluster.

9. A non-transitory computer-readable storage medium storing instructions that, when executed by one or more processors, cause the one or more processors to perform operations comprising:
- receiving a set of parameters, the set of parameters comprising a density parameter, a size parameter, and a node parameter, wherein the density parameter comprises a plurality of density values that include at least a first density value and a second density value, wherein the first density value and the second density value are different, and wherein the node parameter comprises information associated with a plurality of nodes;
- configuring a first execution cycle of a density variation (DENSVAR) clustering algorithm based on the set of parameters;
- executing the first execution cycle of the DENSVAR algorithm, wherein the first execution cycle comprises:
  - determining a distance between different pairs of nodes of the plurality of nodes;
  - identifying candidate nodes of the plurality of nodes based on the distance determined for the different pairs of nodes and the size parameter;
  - assigning the candidate nodes to one of a plurality of candidate clusters;
  - determining whether each candidate cluster of the plurality of candidate clusters satisfies at least the first density value or the second density value; and
  - identifying a first density cluster based on a first candidate cluster of the plurality of candidate clusters satisfying the first density value and a second density cluster based on a second candidate cluster of the plurality of candidate clusters satisfying the second density value during the first execution cycle; and
- transmitting information associated with the first density cluster and the second density cluster to a remote device.

10. The non-transitory computer-readable storage medium of claim 9, the operations further comprising:
- identifying additional density clusters based on whether additional candidate clusters satisfy at least one of the plurality of density values, wherein the first density cluster, the second density cluster, and the additional density clusters include density clusters having different densities; and
- transmitting information associated with the additional density clusters to the remote device.

11. The non-transitory computer-readable storage medium of claim 10, wherein the information associated with the first density cluster and the second density cluster and the information associated with the additional density clusters comprise information that identifies the first density cluster, the second density cluster, and the additional density clusters.

12. The non-transitory computer-readable storage medium of claim 11, wherein the information associated with the first density cluster and the second density cluster and the information associated with the additional density clusters specifies a color coding scheme for displaying information associated with the first density cluster, the second density cluster, and the additional density clusters.

13. The non-transitory computer-readable storage medium of claim 12, wherein the color coding scheme is configured to indicate, at a display of the remote device, at least one characteristic selected from the list consisting of: a density of persons affected by an infectious disease within a geographic region corresponding to the first density cluster, the second density cluster, or one of the additional density clusters; an indication of whether social distancing practices are being followed within the geographic region corresponding to the first density cluster, the second density cluster, or one of the additional density clusters; traffic density within the geographic region corresponding to the first density cluster, the second density cluster, or one of the additional density clusters; consumer demand for one or more products within the geographic region corresponding to the first density cluster, the second density cluster, or one of the additional density clusters; and communication network demand within the geographic region corresponding to the first density cluster, the second density cluster, or one of the additional density clusters.

14. The non-transitory computer-readable storage medium of claim 9, the operations further comprising receiving media content from a data source, wherein at least a portion of the node parameter is derived from the media content.

15. The non-transitory computer-readable storage medium of claim 9, wherein determining whether the candidate cluster satisfies at least one density value of the plurality of density values comprises:
- determining a density of the candidate nodes assigned to the candidate cluster; and
- comparing the density of the candidate nodes assigned to the candidate cluster to at least one of the plurality of density values.

16. A system comprising:
- a memory; and
- one or more processors communicatively coupled to the memory and configured to:
  - receive a set of parameters comprising a density parameter, a size parameter, and a node parameter, wherein the density parameter comprises a plurality of density values that includes at least a first density value and a second density value, wherein the first density value and the second density value are different, and wherein the node parameter comprises information associated with a plurality of nodes;
  - configure a first execution cycle of a density variation (DENSVAR) clustering algorithm based on the set of parameters;
  - execute the first execution cycle of the DENSVAR algorithm to:
  - determine a distance between different pairs of nodes of the plurality of nodes;
  - identify candidate nodes of the plurality of nodes based on the distance determined for the different pairs of nodes and the size parameter;
  - assign the candidate nodes to one of a plurality of candidate clusters;
  - determine whether each candidate cluster of the plurality of candidate clusters satisfies at least the first density value or the second density value; and
  - identify a first density cluster based on a first candidate cluster of the plurality of candidate clusters satisfying the first density value and a second density cluster based on a second candidate cluster of the plurality of candidate clusters satisfying the second density value during the first execution cycle; and
  - transmit information associated with the first density cluster and the second density cluster to a remote device.

17. The system of claim 16, further comprising a database stored at the memory, wherein the information associated with the first density cluster and the second density cluster is transmitted to the remote device based on information stored in the database.

18. The system of claim 16, wherein the one or more processors are configured to:
identify additional density clusters based on whether additional candidate clusters satisfy at least one of the plurality of density values, wherein the first density cluster, the second density cluster, and the additional clusters include clusters having different densities; and
transmit information associated with the additional density clusters to the remote device.

19. The system of claim 16, wherein the one or more processors are configured to transmit cluster data to a user device, wherein the cluster data comprises at least one characteristic selected from the list consisting of: a density of persons affected by an infectious disease within a geographic region corresponding to the first density cluster or the second density cluster; an indication of whether social distancing practices are being followed within the geographic region corresponding to the first density cluster or the second density cluster traffic density within the geographic region corresponding to the first density cluster or the second density cluster; consumer demand for one or more products within the geographic region corresponding to the first density cluster or the second density cluster; and communication network demand within the geographic region corresponding to the first density cluster or the second density cluster.

20. The system of claim 16, wherein the one or more processors are configured to derive at least a portion of the set of parameters based on content received from one or more data sources, and wherein the one or more data sources comprise one or more user devices, cameras, weather sensors, communication networks, or a combination thereof.

* * * * *

UNITED STATES PATENT AND TRADEMARK OFFICE
CERTIFICATE OF CORRECTION

PATENT NO. : 11,468,999 B2
APPLICATION NO. : 16/945170
DATED : October 11, 2022
INVENTOR(S) : Karthik Srinivasan et al.

Page 1 of 1

It is certified that error appears in the above-identified patent and that said Letters Patent is hereby corrected as shown below:

In the Claims

At Column 19, Claim number 1, Line number 64, delete "DENS VAR" and replace with --DENSVAR--.
At Column 24, Claim number 19, Line number 4, delete "cluster traffic" and replace with --cluster; traffic--.

Signed and Sealed this
Twenty-ninth Day of November, 2022

Katherine Kelly Vidal
*Director of the United States Patent and Trademark Office*